US 9,665,918 B2

(12) United States Patent
Ohyu et al.

(10) Patent No.: US 9,665,918 B2
(45) Date of Patent: May 30, 2017

(54) MEDICAL DATA GENERATING APPARATUS AND MEDICAL DATA GENERATING METHOD

(75) Inventors: Shigeharu Ohyu, Yaita (JP); Hitoshi Yamagata, Otawara (JP); Yasuo Sakurai, Nasushiobara (JP); Atsuko Sugiyama, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 619 days.

(21) Appl. No.: 13/478,410

(22) Filed: May 23, 2012

(65) Prior Publication Data

US 2012/0233194 A1    Sep. 13, 2012

Related U.S. Application Data

(63) Continuation of application No. PCT/JP2011/076014, filed on Nov. 11, 2011.

(30) Foreign Application Priority Data

Nov. 22, 2010   (JP) ................................. 2010-260023

(51) Int. Cl.
G06Q 50/22 (2012.01)
G06Q 50/24 (2012.01)

(52) U.S. Cl.
CPC ............. *G06Q 50/22* (2013.01); *G06Q 50/24* (2013.01)

(58) Field of Classification Search
CPC ............................... G06Q 50/22; G06Q 50/24

(Continued)

(56) References Cited

U.S. PATENT DOCUMENTS 7,237,199 B1 * 6/2007 Menhardt et al. ............ 715/736
8,254,649 B2   8/2012 Matsue et al.
(Continued)

FOREIGN PATENT DOCUMENTS

JP    4-285540    10/1992
JP    11-161405   6/1999
(Continued)

OTHER PUBLICATIONS

Japan-language International Search Report for PCT/JP2011/076014, mailed Dec. 27, 2011.
(Continued)

*Primary Examiner* — Syling Yen
(74) *Attorney, Agent, or Firm* — Nixon & Vanderhye P.C.

(57) ABSTRACT

A medical data generating apparatus includes a data processing unit, a work-status data generation unit, a display unit and a work-status restoration unit. The data processing unit acquires medical data from a database to perform data processing. The work-status data generation unit generates work-status data as a data record of medical data. The work-status data indicates a work status of the data processing. The display unit acquires medical data including at least one piece of work-status data from the database to list the acquired pieces of the medical data on a display device together with identification information of the acquired piece of the work-status data. The work-status restoration unit restores a work status of a data processing corresponding to a selected piece of work-status data based on the selected piece of the work-status data.

12 Claims, 6 Drawing Sheets

(58) Field of Classification Search
USPC .............. 707/706, 713, 722, 736, 758, 781, 707/999.002–999.003; 345/419, 619; 600/407; 715/736, 853, 854
See application file for complete search history.

(56) References Cited

U.S. PATENT DOCUMENTS

| 2002/0016718 | A1* | 2/2002 | Rothschild et al. ............... 705/2 |
| 2005/0110788 | A1* | 5/2005 | Turner et al. .................. 345/419 |
| 2011/0105879 | A1* | 5/2011 | Masumoto ............ G06F 19/321 600/407 |

FOREIGN PATENT DOCUMENTS

| JP | 2002-304314 | 10/2002 |
| JP | 2006-75416 | 3/2003 |
| JP | 2003-190102 | 7/2003 |
| JP | 2006-84453 | 3/2006 |
| JP | 2009-022368 | 2/2009 |
| JP | 2010-1228856 | 6/2010 |
| JP | 2010-182018 | 8/2010 |

OTHER PUBLICATIONS

Notification of Transmittal of Translation of the International Preliminary Report on Patentability in PCT/JP2011/076014 mailed Jun. 20, 2013.
Second Office Action issued Nov. 24, 2014, in CN Patent Application No. 201180002851.4.
Office Action issued Mar. 7, 2014, in CN Patent Application No. 201180002851.4.
Office Action issued May 4, 2015 in CN Patent Application No. 201180002851.4.
Office Action issued May 29, 2015 in JP Patent Application No. 2011-244948.
Chinese retrial notice issued Jul. 27, 2016, in CN Patent Application No. 201180002851.4.
CN Retrial Decision issued Dec. 29, 2016 in CN Patent Application No. 201180002851.4.

* cited by examiner

MEDICAL DATA GENERATING APPARATUS AND MEDICAL DATA GENERATING METHOD

CROSS REFERENCE

This is a continuation of Application PCT/JP2011/76014, filed Nov. 11, 2011.

This application is based upon and claims the benefit of priority from Japanese Patent Application No. 2010-260023, filed Nov. 22, 2010; the entire contents of which are incorporated herein by reference.

FIELD

Embodiments described herein relate generally to a medical data generating apparatus and a medical data generating method.

BACKGROUND

Medical data collected in a diagnostic imaging device, such as an X-ray computed tomography (CT) scanner or a magnetic resonance imaging (MRI) scanner, are subjected to various data processing tasks and analyses for the purpose of conducting diagnoses. Taking as an example the case where three-dimensional (3D) image data are collected, the image data are subjected to image processing for generating two-dimensional (2D) image data for display. Such 2D image data includes maximum intensity projection (MIP) image data, multi-planar reconstruction (MPR) image data or volume rendering (VR) image data. Further, processing nuclear magnetic resonance (NMR) signals using magnetic resonance spectroscopy (MRS), frequency spectra can be obtained.

Medical data are processed and analyzed using processing/analysis software, such as dedicated data processing software or data analysis software run on computers. Such processing/analysis software is often provided with a function of storing a work status of the processing/analysis software as a data file and reproducing the work status of the processing/analysis software at the storage time point by referring to the stored work status data.

For example, image analysis software, when it is used as the processing/analysis software, is able to store a work status as a single work status data file and reproduce the same work status. In this case, the work status includes identification information, image processing conditions, data resulting from processing and display status of the image data subjected to image processing.

Normally, the results of data processing or data analysis of medical data are stored in a database. For example, the MIP image data or VR image data generated through image processing are stored in an image database. When frequency spectrum is collected through MRS, numerical data of the frequency spectrum is added to medical image data as additional information, for storage in the medical information database. The medical image data are composed of pixel data for displaying the frequency spectrum in the form of a graph.

The medical data stored in the image database can be displayed in a list using browsing software. Then, desired image data can be selected from the displayed list of image data and transmitted to medical equipment, such as a medical image processor or a medical image server, via a network, using image transmission software.

PRIOR TECHNICAL LITERATURE

[Patent Literature 1] JPA 2005-510324

Work-status data of processing/analysis software for performing various types of data processing and data analyses can be displayed in a list by activating the corresponding processing/analysis software. In other words, the function of registering the work-status data of processing/analysis software and displaying the data in a list is implemented in the processing/analysis software.

Thus, various pieces of processing/analysis software generate a number of work-status data items in data formats specific to the respective pieces of processing analysis software. The generated work-status data are each provided with a file name for management under an operating system (OS), and stored in a file directory specified by the corresponding piece of processing/analysis software. Specifically, the work-status data are each stored in a specified directory as a file on an OS. Diagnostic imaging apparatuses or medical image processors for general use are run by dedicated software, with a user interface being designed therein so that the user cannot directly use the manipulation functions of the OS on the file.

Each piece of processing/analysis software stores the work-status data, in general, in a different directory and in a different format. Therefore, the stored work-status data can be displayed only by the processing/analysis software, per se, that has stored the data. For this reason, once the work-status data of several pieces of processing/analysis software are stored, the user cannot collectively determine the stored work-status data. In other words, the user cannot collectively determine the work-status data of different pieces of processing analysis software.

On the other hand, medical data, such as diagnostic image data, are stored for management in a database for each study. The user may refer to a list of medical data belonging to one study to schedule work, and then may carry out the work, such as interpretation of the diagnostic images. However, in spite of the fact that work-status data of pieces of processing/analysis software are stored, the work-data cannot be referred to together with the list of the medical data. This makes the user's scheduling of work complicated. In other words, the user is not able to collectively determine the medical data and the work-status data of the pieces of processing/analysis software.

In addition, there is a problem that work-status data cannot be selected unless the corresponding processing/analysis software is activated. Thus, in order to determine what data are present as work-status data stored in the past in certain processing/analysis software, the processing/analysis software that stored the work-status data has to be activated once to display a list of the work-status data. In other words, although each piece of processing/analysis software has the conventional function of displaying a list of work-status data, the work-status data cannot be displayed in a list unless the processing/analysis software is activated.

Further, image transmission software is designed to define and transmit image data having a common data structure among data stored in the image database. Thus, image transmission software is not capable of determine the work-status data having unique data structures specific to the respective pieces of processing/analysis software. As a result, it is difficult to provide a function of transmitting work-status data of pieces of processing/analysis software to the image transmission software. In other words, work-status data cannot be externally outputted using an existing transmission system.

The present invention has as its object to provide a medical data generating apparatus which is capable of storing a work status of data processing in the form of work-status data, which data processing is performed for medical data, such as medical image data, thereby enabling effective scheduling of diagnostic works using the stored work-status data, and to provide a medical data generating method.

BRIEF DESCRIPTION OF THE DRAWINGS

FIG. 3 is a diagram illustrating a first example in which medical data including work-status data are listed in a display device of the medical data generating apparatus illustrated in FIG. 1;

FIG. 4 is a diagram illustrating a second example in which medical data including work-status data are listed in a display device of the medical data generating apparatus illustrated in FIG. 1;

DETAILED DESCRIPTION

Figure 1:
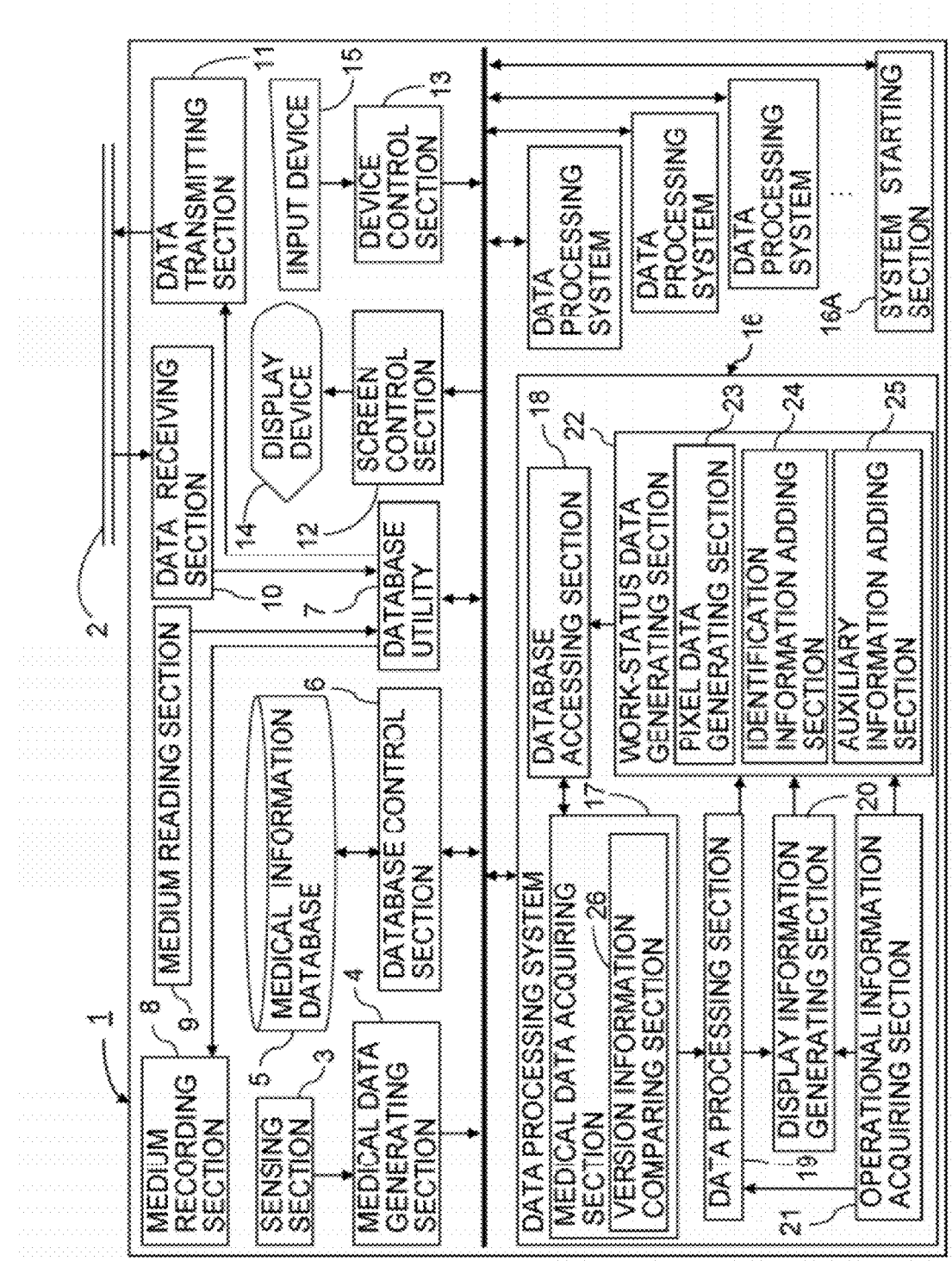
FIG. 1 is a functional block diagram illustrating a medical data generating apparatus related to an embodiment of the present invention.

In general, according to one embodiment, a medical data generating apparatus includes a data processing unit, a work-status data generation unit, a display unit and a work-status restoration unit. The data processing unit is configured to acquire a piece of medical data having pixel data from a database to perform data processing. The database stores pieces of medical data as data records according to attributes. Each of the data records has a structure including a patient, a study, a series and an image. The work-status data generation unit is configured to generate a piece of work-status data as a data record of medical data. The work-status data indicates a work status of the data processing. The data record of the medical data has information for specifying a patient and a study, identification information of the work-status data and pixel data that can be recorded in the database and displayed as an image. The display unit is configured to acquire pieces of medical data including at least one piece of work-status data from the database to list the acquired pieces of the medical data on a display device together with identification information of the acquired piece of the work-status data. The work-status restoration unit is configured to restore a work status of a data processing corresponding to a selected piece of work-status data based on the selected piece of the work-status data. The piece of the work-status data is selected from the listed pieces of the medical data.

Further, according to one embodiment, the medical data generating apparatus includes a data processing unit, a work-status data generation unit, a display unit and a work-status restoration unit. The data processing unit is configured to acquire a piece of medical data having pixel data from a database to perform data processing. The database stores pieces of medical data as data records according to attributes. Each of the data records has a structure including a patient, a study, a series and an image. The work-status data generation unit is configured to generate a piece of work-status data as a data record of medical data. The work-status data indicates a work status of the data processing. The data record of the medical data has information for specifying a patient and a study together with identification information of the work-status data. The data record of the medical data can be recorded in the database. The display unit is configured to acquire pieces of medical data including at least one piece of work-status data from the database to list the acquired pieces of the medical data on a display device together with identification information of the acquired piece of the work-status data. The work-status restoration unit is configured to restore a work status of a data processing corresponding to a selected piece of work-status data based on the selected piece of the work-status data. The piece of the work-status data is selected from the listed pieces of the medical data.

Further, according to one embodiment, a medical data generating method includes: acquiring a piece of medical data having pixel data from a database to perform data processing; generating a piece of work-status data as a data record of medical data having information for specifying a patient and a study, identification information of the work-status data and pixel data that can be recorded in the database and displayed as an image; acquiring pieces of medical data including at least one piece of work-status data from the database to list the acquired pieces of the medical data on a display device together with identification information of the acquired piece of the work-status data; and restoring a work status of a data processing corresponding to a selected piece of work-status data, from the listed pieces of the medical data, based on the selected piece of the work-status data. The database stores pieces of medical data as data records according to attributes. Each of the data records has a structure including a patient, a study, a series and an image. The work-status data indicates a work status of the data processing.

With reference to the accompanying drawings, hereinafter is described a medical data generating apparatus and a medical data generating method related to an embodiment of the present invention.

FIG. 1 is a functional block diagram illustrating the medical data generating apparatus related to the embodiment of the present invention.

A medical data generating apparatus 1 is an apparatus that generates medical data, such as medical image data or medical analytical data, and displays the generated medical data. Examples of the medical data generating apparatus 1 include nuclear medicine diagnostic devices, such as ultrasonic diagnostic devices, X-ray CT scanners, MRI scanners, positron emission computed tomography (PET) scanners or single photon emission computed tomography (SPECT) scanners, or diagnostic imaging devices, such as X-ray diagnostic devices, as well as medical data processors for processing medical data generated in a diagnostic imaging device, or medical data servers having a function of processing data, such as a function of processing images. Description here is given taking as an example the case where the medical data generating apparatus 1 serves as a diagnostic imaging device connected to a network 2.

The medical data generating apparatus 1 includes a sensing section 3, medical data generating section 4, medical information database 5, database control section 6, database utility 7, medium recording section 8, medium reading section 9, data receiving section 10, data transmitting section 11, screen control section 12, device control section 13, display device 14, input device 15 and a plurality of data processing systems 16. Each of the data processing systems 16 includes a medical data acquiring section 17, database accessing section 18, data processing section 19, display information generating section 20, operational information acquiring section 21 and work-status data generating section 22. Further, the work-status data generating section 22 includes a pixel data generating section 23, identification information adding section 24 and auxiliary information adding section 25. The medical data acquiring section 17 includes a version information comparing section 26. The medical data generating apparatus 1 is provided with a system starting section 16A for identifying and starting the plurality of data processing systems 16.

Components for processing digital signals of the medical data generating apparatus 1 can be established by having a computer read the programs. However, dedicated circuits may be used to configure a part or all of the components.

The sensing section 3 is composed of hardware that collects data from a subject. For example, the hardware serves as an ultrasonic transducer, a radio frequency (RF) coil and a radiation detector suitable for the type of the diagnostic imaging device concerned. The medical data generating section 4 has a function of generating medical data, such as diagnostic image data, by processing data collected by the sensing section 3.

The medical information database 5 is a relational database having a hierarchical structure including patients, studies, series and images to record medical data, such as diagnostic imaging data. Specifically, the medical information database 5 is ensured to store a plurality of medical data each having pixel data as an attribute of image data having a structure including a patient, a study, a series and an image suitable for attributes.

For example, when the medical data is contrast-enhanced image data, the pixel data for displaying the contrast-enhanced data are recorded as a data attribute in the medical information database 5. When the medical data is a frequency spectrum of MR signals obtained through MRS processing, the pixel data for displaying the frequency spectrum in the form of a graph are recorded as a data record in the medical information database 5. In other words, the medical data recorded in the medical information database 5 are administered as image data composed of pixel data.

The database control section 6 has a writing function of recording medical data in the medical information database 5, as well as a function of reading desired medical data by searching through the medical data recorded in the medical information database 5 and a function of deleting medical data recorded in the medical information database 5.

The database control section 6 may be ensured to record in any directory a part of medical data, as a data file on the OS of the computer configuring the medical data generating apparatus 1. In this case, the medical information database 5 stores a file name of the data file and information for defining the directory in which the data file is stored, as a part of the data record.

The database utility 7 has a function of executing various types of processing using the medical data recorded in the medical information database 5 by providing instruction information to the database control section 6. For example, the database utility 7 has a function of having the display device 14 display a list of the medical data recorded in the medical information database 5 by providing instruction to the database control section 6, a function of having the display device 14 display desired medical data as an image among the plurality of medical data listed according to the instruction information inputted from the input device 15, and a function of providing desired medical data among the plurality of medical data listed according to the instruction information inputted from the input device 15, to a predetermined component. Further, the database utility 7 has a function of having a list displayed, the list showing medical data generated in the medical data generating section 4, medical data received via the network 2 and medical data read from a recording medium, such as a CD (compact disc), and a function of recording the medical data selected from the list into the medical information database 5.

Specifically, the database utility 7 may be given instruction information to display a list by the input device 15, together with information specifying each of the hierarchical levels, such as a patient, a study and a series. In this case, the database utility 7 provides an instruction for locating the medical data having the specific attribute to the database control section 6. Then, the database utility 7 generates list information for displaying a list which shows the medical data obtained from the database control section 6 as a result of the location, and allows the display device 14 to output the generated list information via the screen control section 12. Thus, the medical data having the specific attribute can be extracted from the medical information database 5 to have the display device 14 displayed the data in a list.

Further, the database utility 7 may be inputted with information regarding selection of medical data from the input device 15, together with information that instructs display of the selected medical data. In this case, the database utility 7 acquires the pixel data that compose the selected medical data from the medical information database 5 via the database control section 6 and allows the display device 14 to output the acquired pixel data via the screen control section 12. Thus, the desired medical data recorded in the medical information database 5 are selected and displayed on the display device 14.

Furthermore, the database utility 7 may be inputted, from the input device 15, with information regarding selection of medical data, together with instruction information regarding deletion or transfer of the selected medical data, or writing of the selected medical data into a recording medium. In this case, the database utility 7 provides instruction information to the corresponding components, together with necessary medical data.

For example, when an instruction for deleting medical data is inputted from the input device 15, the database utility 7 provides a deletion instruction to the database control section 6 together with identification information of the medical data. Thus, the desired medical data are selected and deleted from the list of the medical data displayed on the display device 14.

When an instruction for transmitting specific medical data are inputted from the input device 15 together with a transmission destination, the database utility 7 controls the data transmitting section 11 to have the medical data acquired from the medical information database 5 transmitted to the specified transmission destination via the network 2. When an instruction for writing medical data into a recording medium is inputted from the input device 15, the database utility 7 controls the medium recording section 8 to have the medical data acquired from the medical information database 5 converted to a data file and outputted to the recording medium.

On the other hand, the database utility 7 may be inputted with an instruction for acquiring medical data from the input device 15, together with an instruction for displaying a list of the acquired medical data. In this case, the database utility 7 acquires the medical data from corresponding components to have the display device 14 display the medical data in a list. Thus, the medical data generated in the medical data generating apparatus 1 can be displayed in a list. Medical data may be acquired from outside the medical data generating apparatus 1 via a recording medium or the network 2 to have the acquired medical data displayed in a list.

For example, when medical data is acquired via a recording medium, the database utility 7 controls the medium reading section 9 to have it read the medical data in a file format, for conversion into a data record that can be recorded in the medical information database 5. Then, the database utility 7 generates list information for having the medical data displayed in a list and allows the display device 14 to display the generated list information. When medical data is acquired via the network 2, the database utility 7 controls the data receiving section 10 to have it received the medical data transmitted via the network 2. Then, the database utility 7 generates list information for having the received medical data displayed in a list and allows the display device 14 to display the generated list information.

Thus, in addition to the medical data generated by the medical data generating apparatus 1, the medical data in a file format stored in a recording medium and the medical data received from a different medical system via the network 2 can be displayed in a list on the display device 14. Then, desired medical data among the medical data displayed in a list can be added to the medical information database 5.

Specifically, the database utility 7 is inputted with information regarding selection of medical data from the input device 15, together with instruction information for storing selected medical data in the medical information database 5. Then, the database utility 7 provides an instruction for writing the selected medical data into the medical information database 5 to the database control section 6, together with an identification of the corresponding medical data. Thus, desired medical data can be selected from the medical data displayed in a list on the display device 14 through the operation of the input device 15 and recorded in the medical information database 5.

The medium recording section 8 has a function of acquiring, from the medical information database 5, a data record of the medical data corresponding to the identification information acquired from the database utility 7, for conversion into a data file of medical data which is in conformity with a data conversion standard. The medium recording section 8 also has a function of writing the converted medical data in a file format into a recording medium.

The medium reading section 9 has a function of reading, from a recording medium, medical data in a file format which is in conformity with the data conversion standard to generate a data record of the medical data, and informing the database utility 7 of the identification information of the generated data record of the medical data.

The data receiving section 10 has a function of receiving medical data transmitted from a different medical system, such as a medical image processor or a medical image server, via the network 2, and a function of providing the identification information of the received medical data to the database utility 7.

The data transmitting section 11 has a function of acquiring, from the medical information database 5, medical data corresponding to the identification information acquired from the database utility 7, for transmission to a transmission destination acquired from the database utility 7 via the network 2.

Medical data are transmitted based on a normal communication standard, such as DICOM (digital imaging and communication in medicine), so that the data record of the transmitted medical data can be used in a different medical system. Similarly, medical data to be received in the data receiving section 10 are transmitted from a different medical system based on such a normal communication standard.

Accordingly, the data receiving section 10 has a function of converting medical data of the communication standard into a data record of medical data, which can be recorded in the medical information database 5. On the other hand, the data transmitting section 11 has a function of converting a data record of medical data into medical data of the communication standard.

Each of the data processing systems 16 serves as a system for performing data processing including processing of images or analysis of medical data, such as of diagnostic image data. Each data processing system 16 is established when dedicated processing/analysis software specific to each type of data processing is read and run by a computer. Accordingly, the data processing systems 16 are installed in the medical data generating apparatus 1 by a number equal to the number of types of data processing. Specifically, the individual data processing systems 16 serve as systems for acquiring medical data from the medical information database 5 to perform data processing tasks which are different from each other. It should be appreciated that a single data processing system 16 may perform different data processing tasks.

Examples of data processing tasks include image processing, such as MIP processing, MPR processing, VR processing and functional MRI processing, or image analysis processing, such as cerebral perfusion analysis processing, or data analysis processing, such as MRS processing.

In the cerebral perfusion analysis processing, a contrast agent is injected into a subject to collect time-series contrast-enhanced image data. Using the contrast-enhanced image data as original data, a time-density curve is obtained for the contrast agent in each pixel. Then, index values of hemodynamic states, such as cerebral blood flow (CBF), cerebral blood volume (CBV) and mean transit time (MTT), are calculated based on the time-density curve in each of the pixels. The calculated index values of the hemodynamic states are placed in each of the pixels to generate CBF image data, CBV image data and MTT image data. In the MRS processing, the intensity of the NMR signals of each frequency is graphed to generate a frequency spectrum. Then, pixel data for displaying the frequency spectrum are generated in the data processing system 16.

The data processing section 19 of the data processing system 16 has a function of performing data processing on original data, such as image data or NMR signals, in accordance with given data processing conditions, and a function of outputting the results of the data processing as processing results data. The conditions of data processing can be inputted to the data processing section 19 via the device control section 13 and the operational information acquiring section 21 by operating the input device 15 through a set-up screen shown on the display device 14.

The display information generating section 20 has a function of generating screen information to be provided for data processing, in accordance with display condition specification information derived from the operational information acquiring section 21, and having the generated screen information displayed on the display device 14 via the screen control section 12. The screen displayed on the display device 14 includes screen information for indicating processing results data, such as CBR image data, CBV image data and a frequency spectrum, which are generated by the data processing section 19, as well as the set-up screen for setting the data processing conditions. When a plurality of pieces of screen information are displayed on the display device 14, these pieces of information can be displayed as a plurality of display pages that can facilitate change of display. Further, the processing results data can be displayed under various display conditions.

For example, when the data processing is the cerebral perfusion analysis processing, the displayed set-up screen of the data processing conditions includes an area in which an artery region that is a target of cerebral perfusion analysis is set as a region of interest (ROI) on a reference image, an area for displaying time-density curves of the contrast agent corresponding to the set ROI, and an area for displaying a 2D CBF image generated from the time-density curves. Further, a processing results screen can display an MR image superposed with a CBF image, or can display an orthogonal-three-cross-section image of a 3D CBF image and a 3D MR image.

The operational information acquiring section 21 has a function of acquiring operational information from the input device 15, such as a mouse or a keyboard, via the device control section 13, and a function of providing the acquired operational information to the components of the data processing system 16. Examples of the operational information acquired by the operational information acquiring section 21 from the input device 15 include information for specifying a display mode, information for specifying display data, information for specifying a display page, information for setting an ROI, information for setting data processing conditions and information for setting display conditions of data.

For example, the operational information acquiring section 21 may acquire, from the input device 15, information for specifying a display mode, with which display mode is changed from a 2D display mode to an orthogonal-three-cross-section display mode, or vice versa, or information for switching display data, with which display data is switched from real part data of a frequency spectrum to imaginary part data thereof, or vice versa. In this case, the operational information acquiring section 21 provides the acquired information to the display information generating section 20. Thus, the display status, such as a display mode and display data, of the screen displayed on the display device 14 can be changed. Similarly, the operational information acquiring section 21 may acquire, from the input device 15, information for instructing change of display page. In this case, the operational information acquiring section 21 provides the information for instructing change of display page to the display information generating section 20. Thus, the specified display page can be shown on the display device 14.

In addition, the operational information acquiring section 21 may acquire, from the input device 15, information for setting display conditions, such as enlargement, scroll, rotation or change of slicing position of an image shown on the display device 14, or information for instructing display of various statistical data in an ROI. In this case, the display information generating section 20 is ensured to generate image data to be outputted to the display device 14, in accordance with the inputted information.

Furthermore, the operational information acquiring section 21 may acquire, from the input device 15, information for setting data processing conditions, or instruction information for data processing, such as an instruction for starting data processing. In this case, the operational information acquiring section 21 is ensured to provide the necessary information to the data processing section 19.

The work-status data generating section 22 has a function of generating work-status data as a data record, which indicate a work-status of the data processing performed in the data processing system 16. The data record includes information for defining a patient and a study and identification information of work-status data, and also includes medical data having pixel data as components that can be recorded in the medical information database 5 and can be displayed as an image. Specifically, similar to diagnostic image data, work-status data are generated as a data record which can be recorded in the medical information database 5 that has a hierarchical structure including patients, studies, series and images. Thus, work-status data include attribute for specifying a patient, a study, a series and an image, to which the work-status data belong.

The medical data generating apparatus 1 includes a plurality of data processing systems 16. Accordingly, the plurality of data processing systems 16 include the respective plurality of work-status data generating sections 22. These work-status data generating sections 22 generate work-state data as respective data records which indicate work statuses of data processing tasks which are different from each other.

More specifically, each work-status data generating section 22 is configured to acquire various data indicating work status of the data processing system 16 from the data processing section 19, the display information generating section 20 and the operational information acquiring section 21. Then, based on the acquired data, the work-status data generating section 22 is ensured to generate work-status data as a data record which belongs to the same patient and study as those to which the original data that is a target of data processing belong.

Examples of the data indicating a work status of the data processing system 16 include: definition information, such as an ID, for referring to the original data that is a target of data processing, or for referring to the original data of the data processing; processing condition data indicating various conditions of data processing; processing results data obtained as a result of the data processing; information for setting an ROI, which is indicated on the display device 14; and display status data indicating display status, such as a display mode, a display page and display conditions, of a screen.

Further, the work-status data additionally include pixel data, identification information and auxiliary information. These pixel data, identification information and auxiliary information are additionally provided so that the work-status data can be recorded in the medical information database 5. Also, these data are additionally provided so that a list of information for the operator to determine the information of the stored work-status data is generated.

The pixel data generating section 23 of the work-status data generating section 22 has a function of generating work-state data recorded as a data record in the medical information database 5. The work-status data recorded in the medical information database 5 can be treated in the database utility 7 in a manner similar to medical data, such as diagnostic image data. Accordingly, the identification information of the work-status data may be added to the list shown on the display device 14. Further, the pixel data of the work-status data can be shown on the display device 14 in a manner similar to the pixel data of a diagnostic image.

Preferably, the pixel data of the work-status data are used for data for displaying the work-status data as an iconic figure on the display device 14. In this case, it is important that each iconic figure indicating work-status data has a different design according to the type of the data processing. Thus, the user is able to know the type of the stored work-status data from the iconic figure. This enhances the convenience for the user. Alternatively, the pixel data representing an image, which have been obtained as a result of a data processing, may be used as the pixel data of work-status data. In this case as well, the pixel data, with an iconic figure unique to the type of the data processing being added to the processed image, may be used as the pixel data of the work-status data. Thus, the user's convenience is enhanced.

The identification information adding section 24 has a function of adding identification information to the work-status data. The identification information is used for distinguishing work-status data from medical data other than the work-status data. The identification information of the work-status data may include the information for defining the type of the data processing, as well as version information of the data processing algorithm used for the data processing of the type.

For example, the identification information may be defined on the basis of the type of medical data, such as "work-status data of MRS processing", "work-status data of cerebral perfusion analysis processing" and "diagnostic image data", for addition to the medical data including the work-status data.

The auxiliary information adding section 25 has a function of optionally adding desired information as additional information to work-status data. Thus, information which the user considers to be convenient can be added to the work-status data.

For example, when cerebral perfusion analysis processing is performed, pieces of auxiliary information may be added to the work-status data. In this case, the pieces of auxiliary information include the time of performing the analysis calculation, the calculation process set for the analysis calculation, the types of images, such as a local cerebral blood flow image and a peak-time image, subjected to calculation, the time of storing the work-status data, and the series number for defining the original data of analysis.

Such work-status data including pixel data, identification information and auxiliary information are recorded as medical data in the medical information database 5 and are treated by the database utility 7 as targets to be operated. For example, work-status data can be shown in a list on the display device 14 together with other medical data, such as diagnostic image data, or can be used for restoring each work-status of the corresponding data processing.

Figure 2:
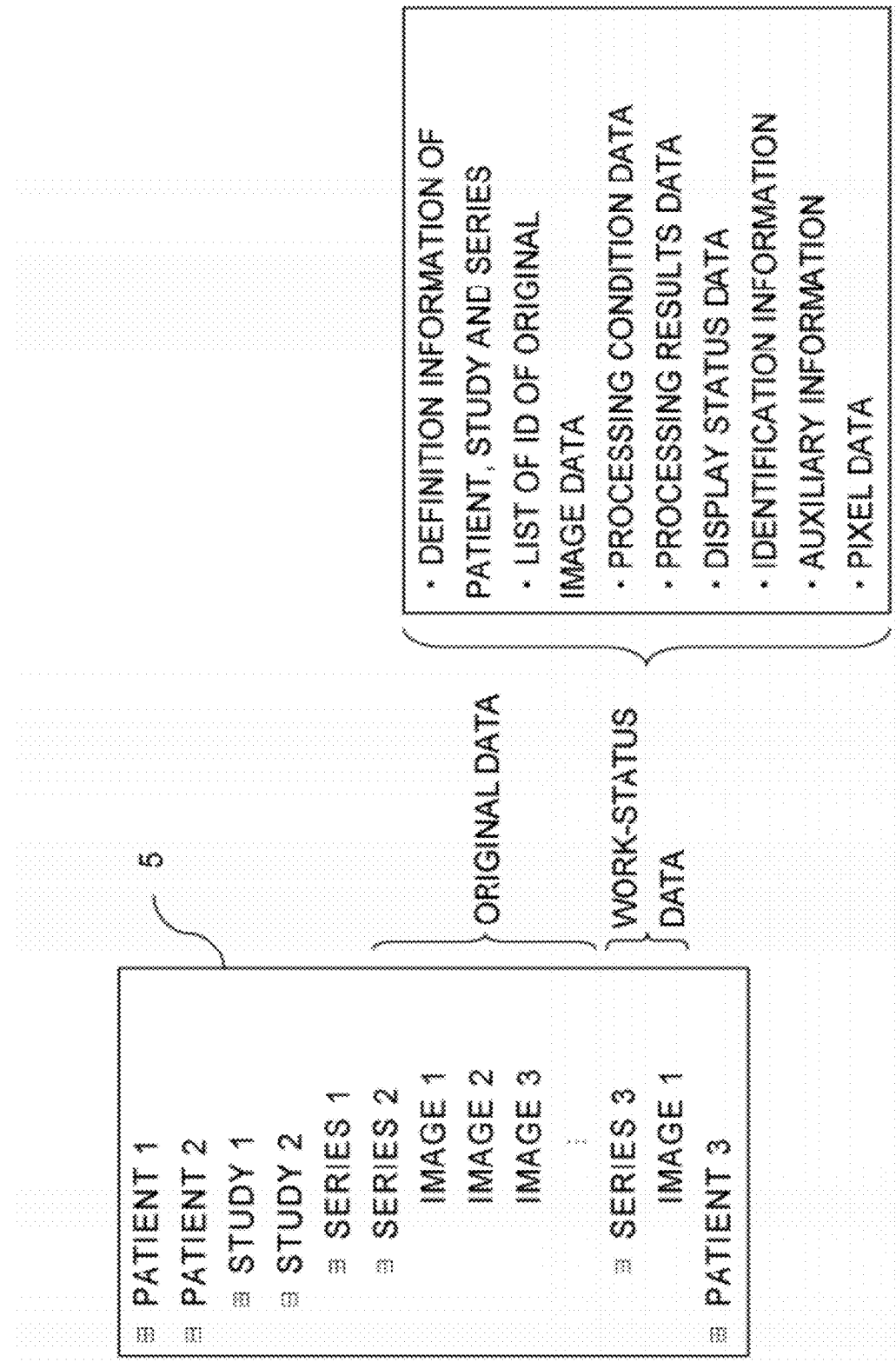
FIG. 2 is a schematic diagram illustrating a hierarchical structure of a medical information database illustrated in FIG. 1 and illustrating particulars of work-status data stored, similar to diagnostic image data, as medical data.

FIG. 2 is a schematic diagram illustrating the hierarchical structure of the medical information database 5 illustrated in FIG. 1, and work-status data stored as medical data in a manner similar to diagnostic image data.

As shown in FIG. 2, the medical information database 5 is recorded with medical data as data records in a hierarchical structure including patients, studies, series and images. For example, let us discuss the case where the data processing system 16 performs data processing using a plurality of diagnostic image data, as original image data, which belong to patient 2, study 2 and series 2 of FIG. 2. In this case, the work-status in the data processing system 16 can be stored in the medical information database 5 as work-status data.

In this regard, the work-status data is stored in the medical information database 5 as a data record with attributes of patient 2 and study 2 which are identical with the patient and the study to which the original image data subjected to data processing belong. In the example of FIG. 2, the work-status data is recorded as a data record of series 3. Also, the pixel data of the work-status data is recorded at the hierarchical level of image as image 1 belonging to series 3.

As shown in FIG. 2, the work-status data may include such parameters as definition information of a patient, a study and a series, as well as an ID list of original image data, processing condition data, processing results data, display status data, identification information, auxiliary information and pixel data.

Such work-status data may be converted to medical data of DICOM communication standard by the data transmitting section 11 and the data receiving section 10, for transmission/reception to/from external medical equipment.

When work-status data is converted to medical data of DICOM standard, the definition information of a patient, a study and a series is converted to data that can be identified by a standard tag. Further, the processing condition data, processing results data, display status data, identification information and auxiliary information can be converted to data that can be identified by a private tag. Also, the pixel data can be converted to data that can be identified by an image tag. The ID list of the original image data may be converted to data that can be identified by a standard tag or a private tag. The same applies to the case where medical data of DICOM standard is converted to a data record of work-status data that can be stored in the medical information database 5.

The work-status data as shown in FIG. 2 can be shown in a list on the display device 14 together with other medical data, under the operation of the database utility 7. Specifically, the database utility 7 is able to acquire a plurality of medical data including work-status data from the medical information database 5 to display the acquired data in a list on the display device 14 together with identification information of the work-status data.

Figure 3:
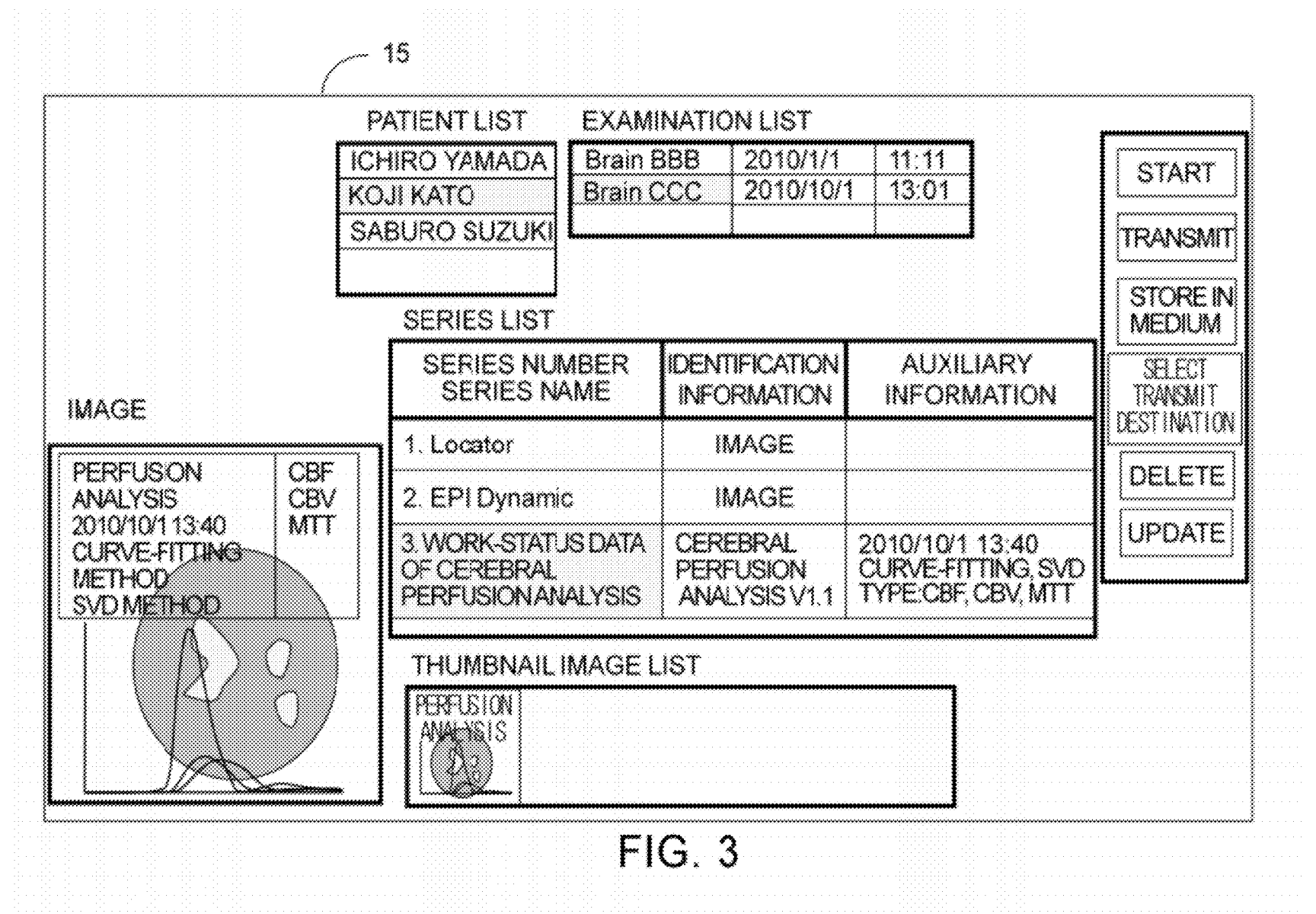
Figure 4:
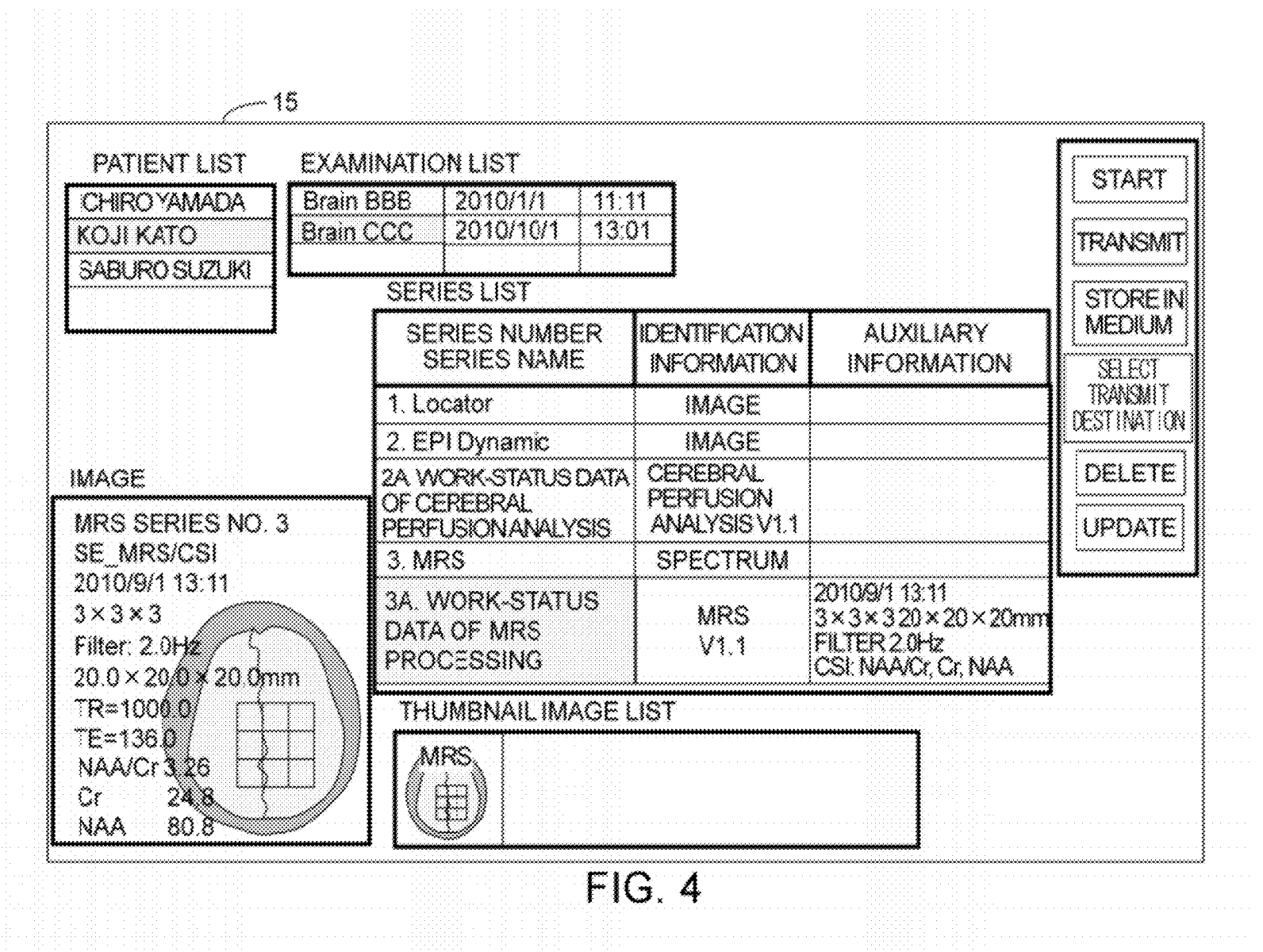

FIG. 3 is a diagram illustrating a first example in which a list of medical data including work-status data is shown on the display device 14 of the medical data generating apparatus 1 illustrated in FIG. 1. FIG. 4 is a diagram illustrating a second example in which a list of medical data including work-status data is shown on the display device 14 of the medical data generating apparatus 1 illustrated in FIG. 1.

As shown in FIGS. 3 and 4, the display device 14 displays, in a selectable manner, a patient list, a study list, a series list and an image list under the operation of the database utility 7. The image list can display a thumbnail image of pixel data composing the medical data. The medical data belonging to selected items are extracted and displayed in a list. In the examples shown in FIGS. 3 and 4, the selected items are highlighted. The screen is configured such that the pixel data of the medical data selected from the image list can be displayed in an image display column on the left.

Work-status data, being treated as medical data including pixel data, is shown in the series list in the same manner as the diagnostic image data. Work-status data is generated as a data record belonging to a patient and a study, which are identical with those of the original data subjected to data processing. Accordingly, when a series list of medical data belonging to a certain patient and a certain study is displayed, the work-status data of the data processing and the original data subjected to the data processing are listed as a data record having an identical patient attribute and an identical study attribute.

In the example shown in FIG. 3, the work-status data in cerebral perfusion analysis processing is indicated in the series list as medical data of series No. 3. Thus, it is easily understood that the work-status data of the cerebral perfusion analysis processing indicate the work status in a cerebral perfusion analysis processing performed for the image data that have been collected by dynamic EPI (echo planar imaging) of series No. 2 belonging to the identical patient and study.

On the other hand, the example shown in FIG. 4 lists a plurality of series of medical data and a plurality of series of work-status data as a series to which identical patient and study belong. Specifically, series Nos. 1 and 2 indicate series of image data, while series No. 3 indicates series of spectrum data. Further, series No. 2A indicates the work-status data of cerebral perfusion analysis processing, while series No. 3A indicates the work-status data of MRS processing.

The series number of the work-status data of cerebral perfusion analysis processing is 2A. Moreover, the work-status data of cerebral perfusion analysis processing is indicated in a lower cell adjacent to the series of image data collected by the EPI dynamic of series No. 2. Thus, because 2 of the series numbers is common and the series numbers are mutually closely indicated in the list, the user is able to easily determine that the work-status data of cerebral perfusion analysis processing are associated with the image data collected by the EPI dynamic of series No. 2.

Similarly, series number of the work-status data of MRS processing is 3A. Moreover, the work-status data of MRS processing is indicated in a lower cell adjacent to the series of frequency spectrum of MR signals collected by the MRS of series No. 3. Thus, because of the common use of the series No. 3 and because of the closely located indication in the list, the user is able to easily determine that the work-status data of MRS processing are associated with the frequency spectrum of MR signals collected by the MRS of series No. 3.

In this way, the database utility 7 is able to display the identification information of work-status data such that the work-status data is identified as being associated with the series to which the original data subjected to the corresponding data processing belong. Specifically, as shown in FIGS. 3 and 4, the database utility 7 is able to display the identification information of work-status data so as to be located close to the identification information of the series to which the original data subjected to the corresponding data processing belong. Alternatively, the database utility 7 is able to display the identification information of the series to which the original data subjected to the data processing corresponding to the work-status data belong, so as to be distinguished from the identification information of the series to which the image data not subjected to the data processing belong.

Further, as shown in FIGS. 3 and 4, identification information and auxiliary information to be added to work-status data can be indicated in the series list. For example, according to FIG. 3, the series list allows easy understanding of not only the version information of algorithm used for the cerebral perfusion analysis processing, but also the auxiliary information including the time and date of performing the cerebral perfusion analysis processing, the calculation process, such as SVD (singular value decomposition) process, used for the calculation, the types of generated images, such as CBF, CBV and MTT. On the other hand, in FIG. 4 as well, the series list allows easy acknowledgment of detailed auxiliary information, such as conditions of MRS processing or conditions of collecting the original data.

Similar to the pixel data of diagnostic image data, the pixel data of work-status data can be shown in the image list as a thumbnail image in a selectable manner. For example, in the example shown in FIG. 3, the work-status data of the cerebral perfusion analysis processing of series No. 3 is selected from the series list. On the other hand, in the example shown in FIG. 4, the work-status data of the MRS processing of series No. 3A is selected from the series list. Accordingly, the image lists of FIGS. 3 and 4 show the icons of the respective work-status data of the selected series. When the icon of the work-status data is selected, the pixel data of the work-status data can be displayed in the image display column of diagnostic image.

FIGS. 3 and 4 each illustrate an example in which the image display column shows pixel data representing an iconic figure that includes the identification information and auxiliary information of the work-status data as characters. Further, FIGS. 3 and 4 each illustrate an image list that shows a thumbnail image in the form of an iconic figure The thumbnail image in each of FIGS. 3 and 4 indicates that the medical data of the selected series is work-status data. Thus, the user is able to easily determine whether the medical data shown in the image list is diagnostic image data or work-status data.

Further, as shown in FIGS. 3 and 4, the iconic figure indicating that the medical data is work-status data is displayed using an iconic figure differently designed for each type of data processing. For example, in the example of FIG. 3, the iconic figure shown in the image display column and the thumbnail image shown in the image list column each include an image of graph and analysis as a part of the figure to indicate that the type of the data processing is cerebral perfusion analysis processing.

As shown in FIG. 3, the pixel data of the work-status data can be generated from the image data obtained as a result of the cerebral perfusion analysis processing. Further, time-density curves resulting from the cerebral perfusion analysis or imaginary time-density curves may be embedded as pixel data. Thus, the user is able to easily determine from the displayed image that the data are the work-status data of cerebral perfusion analysis.

On the other hand, in the example shown in FIG. 4, the iconic figure shown in the image display column and the thumbnail image shown in the image list column each include an image of grid and spectra as a part of the figure to indicate that the type of the data processing is MRS processing. The background image is a MRS plan image used for setting a scanning position when the MRS image is planned to be acquired. The grid figure indicates voxel positions of MRS on the background image. Thus, the user is able to easily understand from the figure not only the fact that the type of the data processing is MRS processing, but also the position of each voxel, the size of each voxel, the number of voxels and the like in the MRS scanning.

In order to enable identification of the type of data processing, the figure such as of a graph may be prepared for each of types of data processing. Alternative to this, however, the figure such as of a graph may be changed according to the individual results of data processing. For example, a miniature figure of the graph, per se, resulting from a cerebral perfusion analysis processing may be used as a part of the figure of the work-status data and the figure of the thumbnail image. In this case, the pixel data generating section 23 is ensured to acquire the processing results data of the data processing from the data processing section 19 for the preparation of pixel data suitable for the processing results data.

With the indication of such a figure, the user is able to see the list of the types and work-status data of all the data processing tasks performed in a certain study. In addition, since the auxiliary information of the work-status data is shown in the series list and in the image display column, even when a plurality of work-status data are stored for a single data processing, the plurality of work-status data can be distinguished from each other.

The work-status data shown in a list can be operated by the database utility 7, similar to other medical data, such as diagnostic image data. The operations of the database utility 7 can be displayed as electronic keys in a selectable manner as shown on the right side of FIG. 3 or 4.

For example, when a transmission destination is specified by clicking the transmission destination selection button, followed by selecting work-status data and clicking the transmission button, the selected work-status data is transmitted to the specified destination via the network 2. In this case, diagnostic image data may be selected together with the work-status data to collectively transmit the work-status data and the diagnostic image data.

Further, when work-status data is selected, followed by clicking the medium storage button, the selected work-status data can be recorded in a file format in a recording medium. In this case as well, the work-status data and diagnostic image data can be collectively recorded in the recording medium.

Specifically, when work-status data is selected from the plurality of medical data shown in a list, electronic keys for accepting a transmission instruction or storage instruction of the selected work-status data may be provided. Then, when transmission of the selected work-status data is instructed by clicking the electronic key, the selected work-status data can be transmitted to a specified destination through the operation of the data transmitting section 11 which is under the control of the database utility 7. Similarly, when storage of the selected work-status data into a recording medium is instructed by clicking the electronic key, the selected work-status data can be stored in a given recording medium through the operation of the medium recording section 8 which is under the control of the database utility 7.

Further, when medical data, such as work-status data or diagnostic image data, is selected, followed by clicking a start button, start instruction information is provided from the database utility 7 to the system starting section 16A, together with the identification information of the selected medical data.

Figure 5:
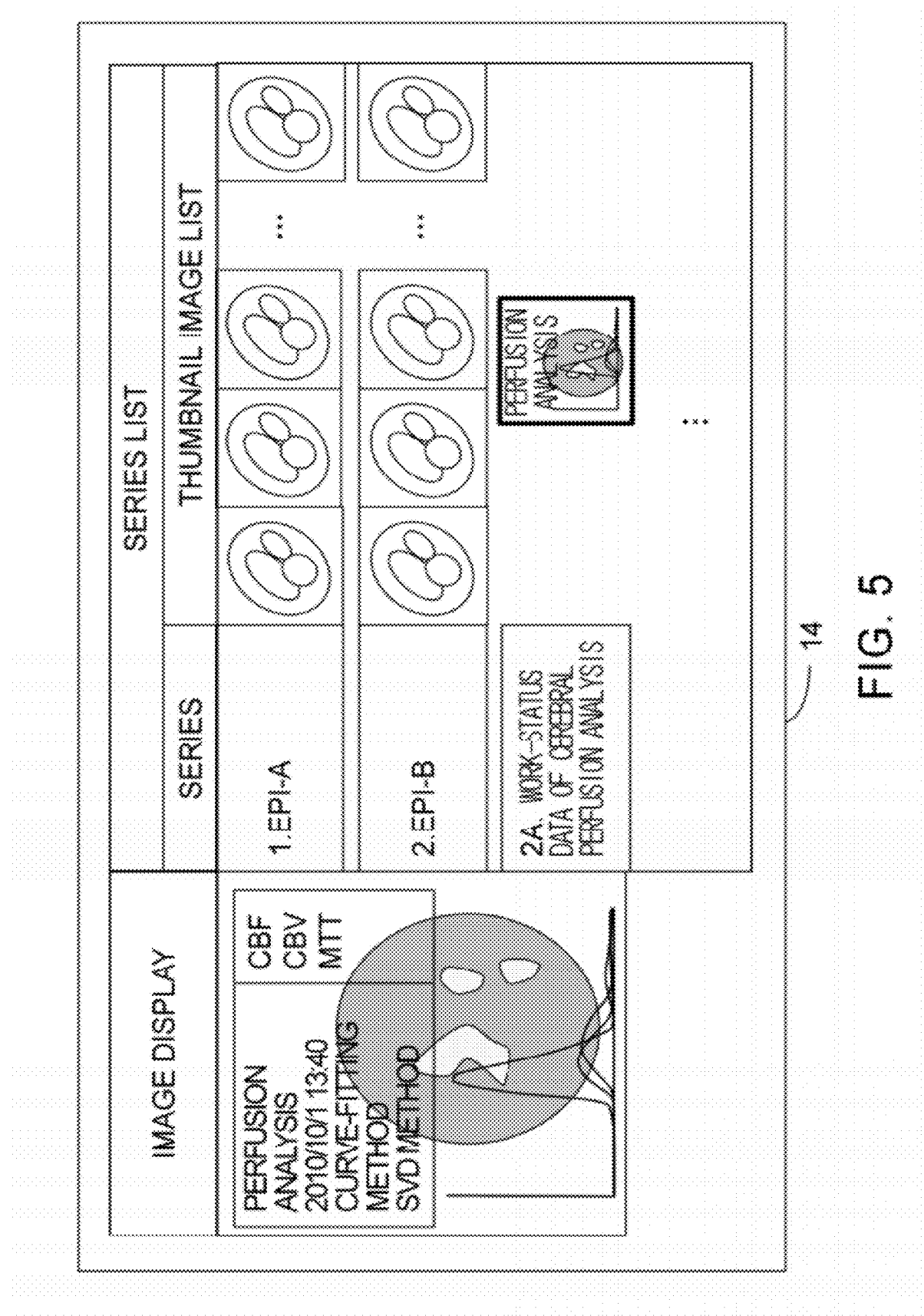
FIG. 5 is a diagram illustrating a third example in which medical data including work-status data are listed in a display device of the medical data generating apparatus illustrated in FIG. 1.

FIG. 5 is a diagram illustrating a third example of a list of medical data including work-status data shown on the display device 14 of the medical data generating apparatus 1 illustrated in FIG. 1.

As shown in FIG. 5, the series list may be represented by a list in which thumbnail images are lined up. Specifically, an image list in which thumbnail images as icons are horizontally lined up may be prepared for each series, and a plurality of such series-specific lists may be vertically arranged for display. In this case, the image lists serve as the components of the series list and thus are able to show, as icons, all the medical data and work-status data belonging to all the series in a selectable manner.

Selected medical data or work-status data can be indicated in the image display column. FIG. 5 shows a state where the icon of the work-status data of series No. 2A is selected. Accordingly, the image display column shows the iconic figure of the work-status data. Further, since the series number of the work-status data is 2A, the work-status data is determined as corresponding to the image data of series No. 2.

In FIG. 5, the patient list, the study list and the electronic keys are omitted, but may be displayed similar to the examples shown in FIGS. 3 and 4.

On the other hand, the medical data acquiring section 17 has a function of acquiring medical data from the medical information database 5 via the database accessing section 18 and the database control section 6, and a function of determining whether the data type of the acquired medical data corresponds to work-status data or corresponds to medical data, such as diagnostic image data, other than work-status data. When work-status data is acquired, the medical data acquiring section 17 has a function of restoring the work status of the data processing system 16 according to the acquired work-status data. When diagnostic data, such as diagnostic image data, is acquired, the medical data acquiring section 17 has a function of providing the acquired diagnostic data to the data processing section 19 as original data of data processing.

Specifically, when medical data is selected from the plurality of medical data listed on the display device 14, the medical data acquiring section 17 is ensured to determine whether the selected medical data is work-status data or diagnostic data, based on the identification information included in the medical data. Further, when the corresponding work-status data is selected from the plurality of medical data listed on the display device 14, the medical data acquiring section 17 is ensured to restore the work status of the data processing that corresponds to the selected work-status data, based on the selected work-status data.

Since the medical data generating apparatus 1 includes a plurality of data processing systems 16, the plurality of data processing systems 16 have the respective plurality of medical data acquiring sections 17. Accordingly, when the corresponding work-status data is selected from the plurality of medical data listed on the display device 14, the work status of the data processing corresponding to the selected work-status data is restored based on the selected work-status data.

The version information comparing section 26 of the medical data acquiring section 17 has a function of making a comparison between versions. Specifically, when a work status is restored according to the selected work-status data, the version information comparing section 26 compares the version of the processing algorithm corresponding to the selected work-status data with the version of the processing algorithm used for the data processing in the data processing system 16.

Then, when the versions of the processing algorithms are identical, the medical data acquiring section 17 is ensured to provide pieces of information, such as identification information of the original data, processing condition data, processing results data and display status data, included in the work-status data, to the respective components of the data processing system 16 for the restoration of the work status. On the other hand, when the versions of the processing algorithms are not identical, the medical data acquiring section 17 is ensured to provide only those pieces of information which are shared between the processing algorithms of different versions from among the pieces of information included in the work-status data, to the respective components of the data processing system 16 for the partial restoration of the work status.

The identicalness of the processing algorithms can be determined by referring to the identification information included in the work-status data.

The pieces of information shared between the processing algorithms having different versions may include identification information of the original data, processing condition data and processing results data. The items of the work status that have not been restored due to the unidentical versions of the processing algorithms may be initialized or may be set to a status which was stored immediately before the current status.

Since the data processing system 16 is permitted to carry out the processing of comparing/determining versions, the work status with respect to the processing algorithm of the current version can be restored using the work-status data stored with respect to the processing algorithm of the previous version. Specifically, the data processing results generated by the processing algorithm of the version in the past can be read into the data processing system 16 that operates with the processing algorithm of the current version. Alternatively, data processing can be re-executed with the processing algorithm of the current version, using the same data processing conditions as those used for the processing algorithm of the version in the past.

Further, when minute changes are introduced to the data processing software used for the data processing system 16, work-status data can be read into the data processing system 16 without being influenced by the changes. Furthermore, among the stored work-status data, appropriate processing can be performed for the data that cannot be dealt with the processing/analysis software of the current version, or for insufficient data. Thus, inappropriate processing results are prevented from being displayed.

The database accessing section 18 has a function of acquiring medical data from the medical information database 5 via the database control section 6. In this case, the database accessing section 18 uses the identification information, such as an ID, of the medical data acquired from the system starting section 16A, for the acquisition of the medical data corresponding to the identification information from the medical information database 5. The database accessing section 18 also has a function of providing the acquired medical data to the medical data acquiring section 17 and a function of registering the work-status data generated by the work-status data generating section 22, as medical data, at the medical information database 5 via the database control section 6.

The system starting section 16A has a function of starting the data processing system 16 corresponding to the data type of the medical data which corresponds to the identification information. This function is carried out when the identification information of the medical data is acquired from the database utility 7 together with start instruction information of the data processing system 16. The system starting section 16A also has a function of providing the identification information of the medical data to the database accessing section 18 of the started data processing system 16. Specifically, when work-status data is selected from the plurality of medical data listed on the display device 14, the system starting section 16A is ensured to identify and start the data processing system 16 corresponding to the selected work-status data, in accordance with the start instruction information and the identification information of the work-status data acquired from the database utility 7.

For example, in the operation screen of the database utility 7 as shown in FIGS. 3 and 4, when the start button is clicked in a state where the icon shown in the image list is selected, start instruction information for the data processing system 16 is provided from the database utility 7 to the system starting section 16A, together with the ID of the medical data corresponding to the icon. Then, the system starting section 16A acquires information indicating the data type of the medical data corresponding to the ID from the medical information database 5 via the database control section 6 and starts the data processing system 16 corresponding to the data type. Then, the system starting section 16A notifies the ID of the medical data as one of starting parameters to the database accessing section 18.

It should be appreciated that the system starting section 18 may directly acquire the start instruction information for the data processing system 16 via the device control section 13 through the operation of the input device 15. Further, the database accessing section 18 may inquire of the database utility 7 to acquire the ID of the medical data from the database utility 7.

The screen control section 12 has a function of updating the screen so that screen information is displayed on the display device 14. This function is carried out when the screen control section 12 acquires the screen information, together with display request information, from the database utility 7 or the display information generating section 20 of each data processing system 16.

The device control section 13 has a function of acquiring operational information from the input device 15, such as a mouse or a keyboard, for distribution to the database utility 7 and the operational information acquiring section 21 of each data processing system 16.

Hereinafter is described the operation and effects of the medical data generating apparatus 1. The description will be given taking as an example the case where an MRI scanner is used to collect time-series contrast-enhanced image data of the head of a subject. In the example, cerebral perfusion analysis processing is performed using the contrast-enhanced image data in a plurality of time phases as original image data to generate CBF image data, CBV image data and MTT image data.

Figure 6:
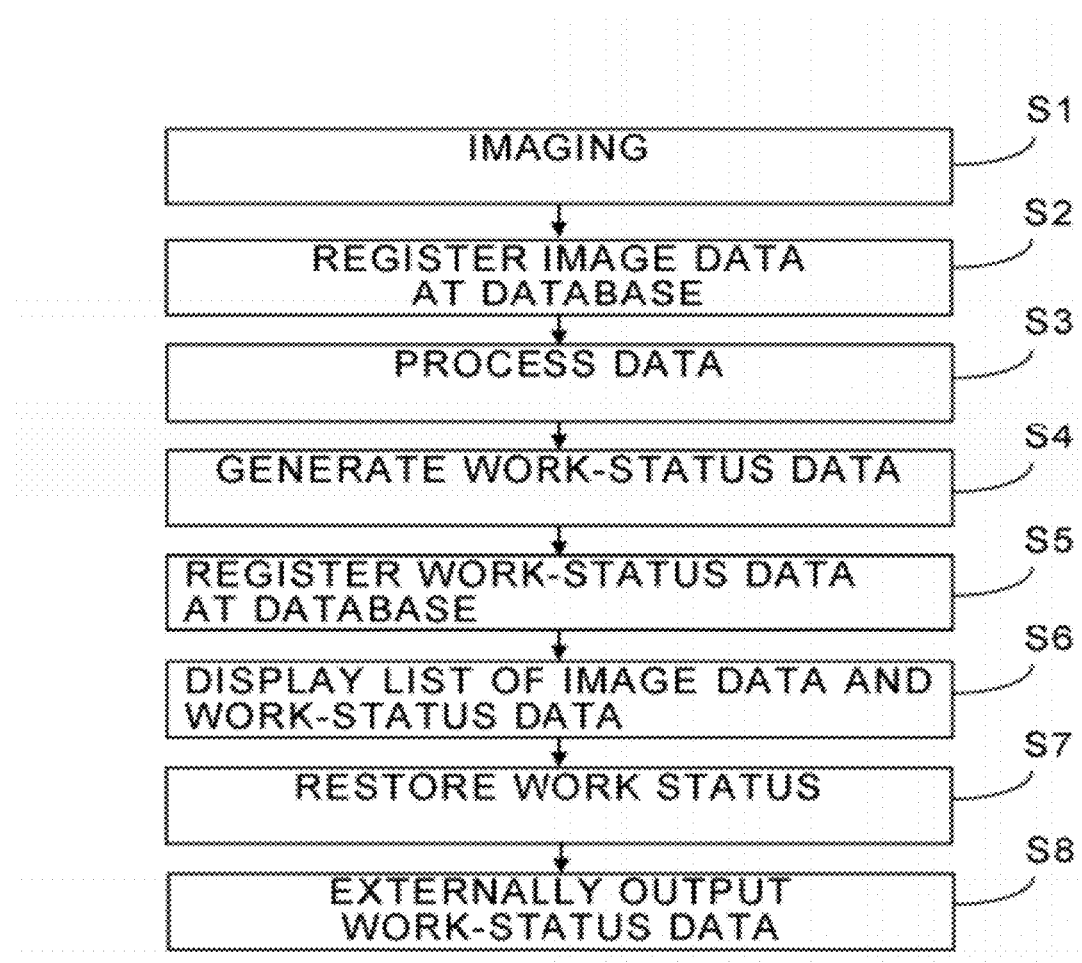
FIG. 6 is a flow diagram illustrating a flow of image processing by collecting diagnostic image data of a subject using the medical data generating apparatus illustrated in FIG. 1.

FIG. 6 is a flow diagram illustrating a flow of collecting diagnostic image data of a subject to perform image processing, using the medical data generating apparatus 1 illustrated in FIG. 1.

First, at step S1, a contrast agent is injected to the subject to carry out imaging using the medical data generating apparatus 1. Specifically, the subject is set in a magnetic field, which is formed of a magnetostatic magnet and a gradient coil. Then, NMR signals generated from the subject are sequentially received by the sensing section 3 having an RF coil. Then, the medical data generating section 4 performs image reconstruction processing for the NMR signals collected by the sensing section 3 to thereby generate contrast-enhanced image data of the subject with a plurality of frames corresponding to the respective plurality of time phases.

Then, at step S2, the contrast-enhanced image data is stored in the medical information database 5. In other words, the database control section 6 acquires the time-series contrast-enhanced image data from the medical data generating section 4 and writes the data into the medical information database 5 as a data record having corresponding patient attribute and study attribute. The contrast-enhanced image data may be displayed in a list by the database utility 7 and then recorded in the medical information database 5.

Then, at step S3, cerebral perfusion analysis processing is performed for the contrast-enhanced image data by the data processing system 16. To this end, the medical data having a patient attribute and a study attribute identical with those of the contrast-enhanced image data are displayed in a list by the database utility 7. Then, when the start button as shown in FIGS. 3 and 4 is clicked in a state where the contrast-enhanced image data is selected from the displayed list, start instruction information is provided from the database utility 7 to the system starting section 16A, together with an ID of the contrast-enhanced image data.

Then, the system starting section 16A starts the data processing system 16 for performing cerebral perfusion analysis processing and notifies the ID of the contrast-enhanced image data to the database accessing section 18 of the started data processing system 16. Then, the database accessing section 18 refers to the ID of the contrast-enhanced image data and acquires the contrast-enhanced image data from the medical information database 5 via the database control section 6. The acquired contrast-enhanced image data are provided to the medical data acquiring section 17 as medical data including identification information of data type.

Then, the medical data acquiring section 17 refers to the identification information of the medical data acquired from the database accessing section 18 and determines that the medical data is the contrast-enhanced image data to be subjected to cerebral perfusion analysis processing. Then, the medical data acquiring section 17 provides the contrast-enhanced image data to the data processing section 19.

On the other hand, the display information generating section 20 allows the display device 14 to display a set-up screen via the screen control section 12. The set-up screen is used for setting data processing conditions, i.e. conditions for the cerebral perfusion analysis processing, such as an ROI and the types of analysis images subjected to calculation. Then, the condition information for the cerebral perfusion analysis processing, such as set-up information of an ROI and the types of analysis images subjected to calculation, are inputted from the device control section 13 to the operational information acquiring section 21, as operational information of the input device 15. The inputted condition information of the cerebral perfusion analysis processing is provided, as processing condition data, from the operational information acquiring section 21 to the data processing section 19.

The data processing section 19 then performs the cerebral perfusion analysis processing using the contrast-enhanced image data as original image data, according to the processing condition data. Thus, CBF image data, CBV image data and MTT image data are generated as processing results data of the cerebral perfusion analysis.

Then, specification information for the display conditions is inputted, together with display instruction information for the processing results data, into the display information generating section 20, as operational information of the input device 15, via the device control section 13 and the operational information acquiring section 21. Upon input of the operational information, the display information generating section 20 generates screen information according to the specified display conditions to display the processing results data acquired from the data processing section 19. The generated screen information is displayed on the display device 14 via the screen control section 12.

Thus, the user is able to observe an analysis image, such as an orthogonal-three-cross-section image or a superimposed image, displayed according to the desired display conditions.

Then, at step S4, when the user inputs an instruction for storing a work status, as operational information of the input device 15, into the work-status data generating section 22, the work-status data generating section 22 acquires data from the individual components of the data processing system 16 to generate the work-status data. The data acquired from the individual components include an ID of the contrast-enhanced image data that is the original image data of the cerebral perfusion analysis processing, processing condition data of the cerebral perfusion analysis, processing results data of the cerebral perfusion analysis, and display status data indicating display status of such images as a CBF image, a CBV image and an MTT image resulting from the processing.

Further, the identification information adding section 24 adds identification information to the work-status data. The identification information includes version information of the processing algorithm used for the cerebral perfusion analysis processing and indicates that the work-status data is of the cerebral perfusion analysis processing. Further, the auxiliary information adding section 25 adds auxiliary information to the work-status data according to the instruction information from the input device 15. The auxiliary information includes the date and time of performing the cerebral perfusion analysis, the calculation method used for the processing and the types of the generated images.

Further, the pixel data generating section 23 generates pixel data to be displayed on the display device 14. The pixel data is generated in the form of an iconic figure using a figure indicative of the data's being work-status data of the cerebral perfusion analysis processing. For example, the pixel data generating section 23 combines the CBV image resulting from the cerebral perfusion analysis with the graph of time-density curves. Further, the pixel data generating section 23 merges the characters indicating the identification information with those of the auxiliary information so as to be displayed as an image, and generates the pixel data.

Then, the work-status data generated in this way is imparted with a patient attribute and a study attribute in the work-state data generating section 22. The imparted patient attribute and the study attribute are identical with those of the contrast-enhanced image data that is the original data subjected to data processing.

Then, at step S5, the work-status data generating section 22 registers the work-status data as medical data at the medical information database 5 via the database accessing section 18 and the database control section 6. Thus, as shown in FIG. 2, the work-status data is stored in the medical information database 5 having a hierarchical structure, as a data record belonging to the patient and the study which are identical with those of the contrast-enhanced image data that is the original data of the cerebral perfusion analysis processing.

Then, the user may terminate the data processing system 16 for performing the cerebral perfusion analysis processing to perform a different work.

Then, at step S6, when an instruction for listing medical data is inputted, at a desired time point, to the database utility 7 together with the information for specifying a patient and a study, as operational information of the input device 15, the database utility 7 allows the display device 14 to display a list of medical data including the work-state data and the contrast-enhanced image data. Thus, a list of medical data as shown in FIG. 3 is displayed on the display device 14.

Then, at step S7, when the start button is clicked, through the operation of the input device 15, in a state where the work-status data is selected, the data processing system 16 for performing the cerebral perfusion analysis processing is started to restore the work status defined by the work-status data.

Specifically, when the start button is clicked, start instruction information for the data processing system 16 is provided, together with an ID of the work-status data, from the database utility 7 to the system starting section 16A. Then, the system starting section 16A starts the data processing system 16 for performing the cerebral perfusion analysis processing and notifies the ID of the work-status data to the database accessing section 18.

Then, the database accessing section 18 refers to the ID of the work-status data and acquires the work-status data from the medical information database 5 via the database control section 6. The acquired work-status data are provided to the medical data acquiring section 17 as medical data including the identification information of the data type.

Then, the medical data acquiring section 17 refers to the identification information of the medical data and determines that the medial data is the work-status data of the cerebral perfusion analysis processing. Further, the version information comparing section 26 refers to the identification information included in the work-status data and compares the version of the processing algorithm corresponding to the work-status data with the version of the processing algorithm in the data processing system 16.

Then, when the versions of the processing algorithms are identical, the medical data acquiring section 17 provides pieces of information included in the work-status data to the respective components of the data processing system 16 to thereby restore the work status. The pieces of information include the identification information of the contrast-enhanced image data, processing condition data, processing results data and display status data.

On the other hand, when the versions of the processing algorithms are not identical, the medical data acquiring section 17 provides only those pieces of information which are shared between the processing algorithms of different versions from among the pieces of information included in the work-status data, to the respective components of the data processing system 16 for the partial restoration of the work status. In this case, the items of the work status that have not been restored are initialized, for example.

Therefore, the user is always able to restore a work status defined not only by the work-status data generated with respect to the algorithms whose versions are identical, but also by the work-status data generated with respect to the algorithms whose versions are not identical.

Then, at step S8, the work-status data may be outputted to the outside of the medical data generating apparatus 1 in order to use the work-status data, as necessary, in a different medical system.

For example, as shown in FIG. 3, when work-status data is selected from the list displayed by the database utility 7, followed by clicking the medium storage button, the database utility 7 notifies the ID of the selected work-status data to the medium recording section 8. Then, the medium recording section 8 acquires the work-status data corresponding to the ID from the medical information database 5 to generate a data file of the work-status data. Then, the medium recording section 8 outputs the data file of the work-status data to a recording medium.

Further, as shown in FIG. 3, when work-status data is selected from the list displayed by the database utility 7, followed by clicking the transmission button, the data transmitting section 11 is activated. Then, the work-status data is transmitted, via the network 2, to a destination specified by clicking the transmission destination selection button.

Thus, the work-status data of the data processing system 16 can be used in a data processing system for performing the corresponding data processing in a different medical system. The version of processing algorithm in the data processing system 16 may be different from the version of the processing algorithm in the data processing system of a different medical system. In this case as well, through the version comparing/determining processing performed by a version information comparing section of the different medical system, only those items of the work-status data among the selected work-status data which are compatible between the versions can be restored.

The medical data generating apparatus 1 as described above is ensured to store pieces of work-status information of various types of data processing performed for medical data. The pieces of work-status information are stored, as data records, in the medical information database 5 having a hierarchical structure. The medical data generating apparatus 1 is also ensured to collectively indicate the stored pieces information in a list, together with such medical data as diagnostic image data, irrespective of the types of data processing.

Thus, according to the medical data generating apparatus 1, the works, such as image processing or image analysis, associated with data processing tasks can be easily scheduled. In other words, the work-status information of the data processing tasks performed in the past can be effectively used for scheduling data processing tasks. Further, the user's convenience is enhanced in various operations.

For example, similar to diagnostic image data, work-status data indicating work-status information of a data processing can be listed on a patient basis and on a study basis. Further, when an icon of work-status data is shown, in an image list, in the form of a figure suitable for the type of data processing, the user can refer to the figure of the icon to determine the type of the data processing corresponding to the work-status data.

Further, work-status data is shown in a list together with original data, as a data record having a patient attribute and a study attribute, which are identical with those of the original data subjected to data processing. Thus, the user is able to easily grasp the type of the performed data processing and the original data subjected to each data processing, based on the list. Then, the user is able to easily schedule the works which are required to be carried in the future.

In addition, work-status data can be treated in a manner similar to other diagnostic image data. Thus, the work-status data can be transmitted to a desired medical system via a network or can be stored in a recording medium, with an operation similar to that for dealing diagnostic image data. In this case, the work-status data can be collectively transmitted or stored together with other diagnostic image data.

Furthermore, the medical data generating apparatus 1 automatically determines whether the medical data is work-status data or diagnostic data, automatically determines the type of the data processing corresponding to the work-status data, and automatically check the version of the processing algorithm. Thus, the user's load of operation can be mitigated. Specifically, if only certain work-status data is selected and a starting instruction is inputted, the corresponding data processing system 16 is automatically started without the necessity of inputting information regarding the medical data's being work-status data or diagnostic data, thereby restoring the work status suitable for the algorithm version.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the embodiment described above includes the medical information database 5 as a component of the medical data generating apparatus 1. Alternatively, however, it may be so configured that the medical information database 5 is connected to the medical data generating apparatus 1 via the network 2. In this case, medical data in the medical information database 5 may be provided to the individual components of the medical data generating apparatus 1 via the database utility 7.

Further, the embodiment described above has been described taking as an example in which pixel data that can be visually displayed are displayed as components of work-status data. Alternative to this, information for identifying work-status data may be shown in a list without using pixel data as components.

What is claimed is:

1. A medical data generating apparatus comprising:
a data processor and memory circuits configured to
acquire diagnostic medical pixel data from a medical information database and perform data processing thereon in accordance with work status data, said medical information database storing diagnostic medical data records that have a hierarchical structure including attributes of the medical pixel data identifying (A) a patient, (B) a study, (C) a series and (D) diagnostic medical image pixel data;
generate work-status data formatted to also have said hierarchical structure and also stored in said medical information database as medical data which is identified as belonging to the same patient and study as respectively corresponding medical pixel data but for a different series that is indicative of work status data, the work-status data indicating a data processing work status of the respectively corresponding medical image pixel data including information organized in said hierarchical structure specifying (a) a patient, (b) a study, (c) series identification information of the work-status data and (d) work-status pixel data that is not only diagnostic medical image pixel data but which includes work-status pixel data that is displayed as an iconic image including predetermined features indicative of a respectively associated type of work-status data;
acquire diagnostic medical data and its respectively corresponding associated work-status data from the database and display a list of the acquired medical data including its work status data together on a display device including the (c) series identification information of the acquired work-status data;
restore data processing work status for the acquired diagnostic medical data corresponding to a selected work-status from the displayed work status data in the list; and
determine whether medical data selected from the listed medical data is work-status data or diagnostic medical data based on identification information included in the selected medical data.

2. A medical data generating apparatus of claim 1, wherein said work-status restoration compares a version of an algorithm previously used for the data processing corresponding to the selected work-status data acquired from the database with a current version of the algorithm corresponding to the selected work-status data and restores only an item of the selected work-status data that is compatible between the versions.

3. A medical data generating apparatus of claim 1, wherein a patient attribute and a study attribute are added to the generated work-status data, the patient attribute and the study attribute being identical with a patient attribute and a study attribute of original diagnostic medical pixel data on which the data processing has been performed.

4. A medical data generating apparatus of claim 1, wherein the data processor and memory are further configured to:
start a data processing program corresponding to the selected work-status data from the listed diagnostic medical data.

5. A medical data generating apparatus of claim 1, wherein the data processor and memory are further configured to:
receive an instruction for transmitting or storing the selected work-status data from the listed medical data; and
transmit or store the selected work-status data in response to the received instruction.

6. A medical data generating apparatus of claim 1, wherein the data processor and memory are further configured to:
perform conversion between work-status data and diagnostic medical data meeting a pre-determined standard communication protocol to transmit and/or receive the converted work-status data.

7. A medical data generating apparatus of claim 1, further comprising:
a database configured to store the work-status data having patient and study attributes, the patient and the study being identical with a patient and a study to which original diagnostic medical data of the performed data processing belong.

8. A medical data generating apparatus of claim 1, wherein identification information of the work-status data is displayed and identified as relating to a series to which original diagnostic medical data subjected to corresponding data processing belong.

9. A medical data generating apparatus of claim 8, wherein identification information of the work-status data is displayed and located close to identification information of a series to which original diagnostic medical data subjected to corresponding data processing belong.

10. A medical data generating apparatus of claim 1, wherein identification information of a series to which original diagnostic medical data subjected to data processing corresponding to the work-status data belong is displayed in a form distinguishable from identification information of a series to which image data not subjected to the data processing belong.

11. A medical data generating apparatus of claim 1, wherein:
mutually different data processing tasks are performed on an original diagnostic medical data set;

pieces of the work-status data are generated as data records respectively, indicating work statuses of the different data processing tasks; and a work status is restored in a data processing task corresponding to the selected piece of the work-status data out of the listed medical data, based on the selected piece of work-status data.

12. A medical data generating method comprising:

acquiring medical diagnostic medical pixel data from a medical information database and performing data processing thereon in accordance with work status data, said medical information database storing medical data records that have a hierarchical structure including attributes of the diagnostic medical pixel data identifying (A) a patient, (B) a study, (C) a series and (D) diagnostic medical image pixel data;

generating work-status data formatted to also have said hierarchical structure and also stored in said medical information database as medical data which is identified as belonging to the same patient and study as respectively corresponding medical pixel data but for a different series that is indicative of work status data, the work-status data indicating a data processing work status of the respectively corresponding medical image pixel data including information organized in said hierarchical structure specifying (a) a patient, (b) a study, (c) series identification information of the work-status data and (d) work status pixel data that is not only diagnostic medical image pixel data but which includes work-status pixel data that is displayed as an iconic image including predetermined features indicating that the generated data is a respectively corresponding type of work-status data;

acquiring diagnostic medical data including its respectively corresponding associated work-status data from the database and listing on a display the acquired work-status data identification information together with its associated diagnostic medical data;

restoring data processing work status for the acquired diagnostic medical data corresponding to a selected work-status displayed in the list; and determining whether medical data selected from the listed medical data is work-status data or diagnostic medical data based on identification information included in the selected medical data.

\* \* \* \* \*